United States Patent [19]

Willemen

[11] Patent Number: 5,731,518

[45] Date of Patent: Mar. 24, 1998

[54] SOLDER FLUXER WITH LIQUID FLUX DENSITY CONTROL

[75] Inventor: Lambertus Petrus Christinus Willemen, Dorst, Netherlands

[73] Assignee: Soltec B.V., Oosterhout, Netherlands

[21] Appl. No.: 609,937

[22] Filed: Feb. 29, 1996

[30] Foreign Application Priority Data

Mar. 3, 1995 [NL] Netherlands ................ 9500426

[51] Int. Cl.$^6$ .................................................. G01N 9/26
[52] U.S. Cl. ............................................................ 73/438
[58] Field of Search ................... 73/438, 442, 445, 73/447, 449

[56] References Cited

U.S. PATENT DOCUMENTS

| | | | |
|---|---|---|---|
| 2,613,681 | 10/1952 | Cooper | 137/4 |
| 3,033,040 | 5/1962 | Piros | 73/438 |
| 3,250,122 | 5/1966 | Doering | 73/438 |
| 3,564,926 | 2/1971 | Chadenson et al. | 73/438 |
| 3,848,618 | 11/1974 | Royse | 73/438 |
| 4,193,303 | 3/1980 | Egnell | 73/438 |
| 4,680,965 | 7/1987 | Weitmann et al. | 73/445 |

FOREIGN PATENT DOCUMENTS

| | | |
|---|---|---|
| 589698 | 6/1925 | France. |
| 2036404 | 12/1970 | France. |
| 2 687 475 | 8/1993 | France. |
| 2 042 957 | 10/1980 | United Kingdom. |

*Primary Examiner*—Christine K. Oda
*Attorney, Agent, or Firm*—Banner & Witcoff, Ltd.

[57] ABSTRACT

An apparatus for applying solder enhancing liquid flux to objects for soldering including a fluxer wherein the density of the liquid flux supplied to the fluxer is controlled by a device for determining the density intermediately a flux storage container, and the fluxer; the density determining device producing an output signal whereby the quantity of diluent supplied to a liquid flux storage container is controlled. The density determining device includes a liquid flux pressure measurer with a vessel extending thereabove which includes an overflow to maintain constant flux liquid level therein.

9 Claims, 1 Drawing Sheet

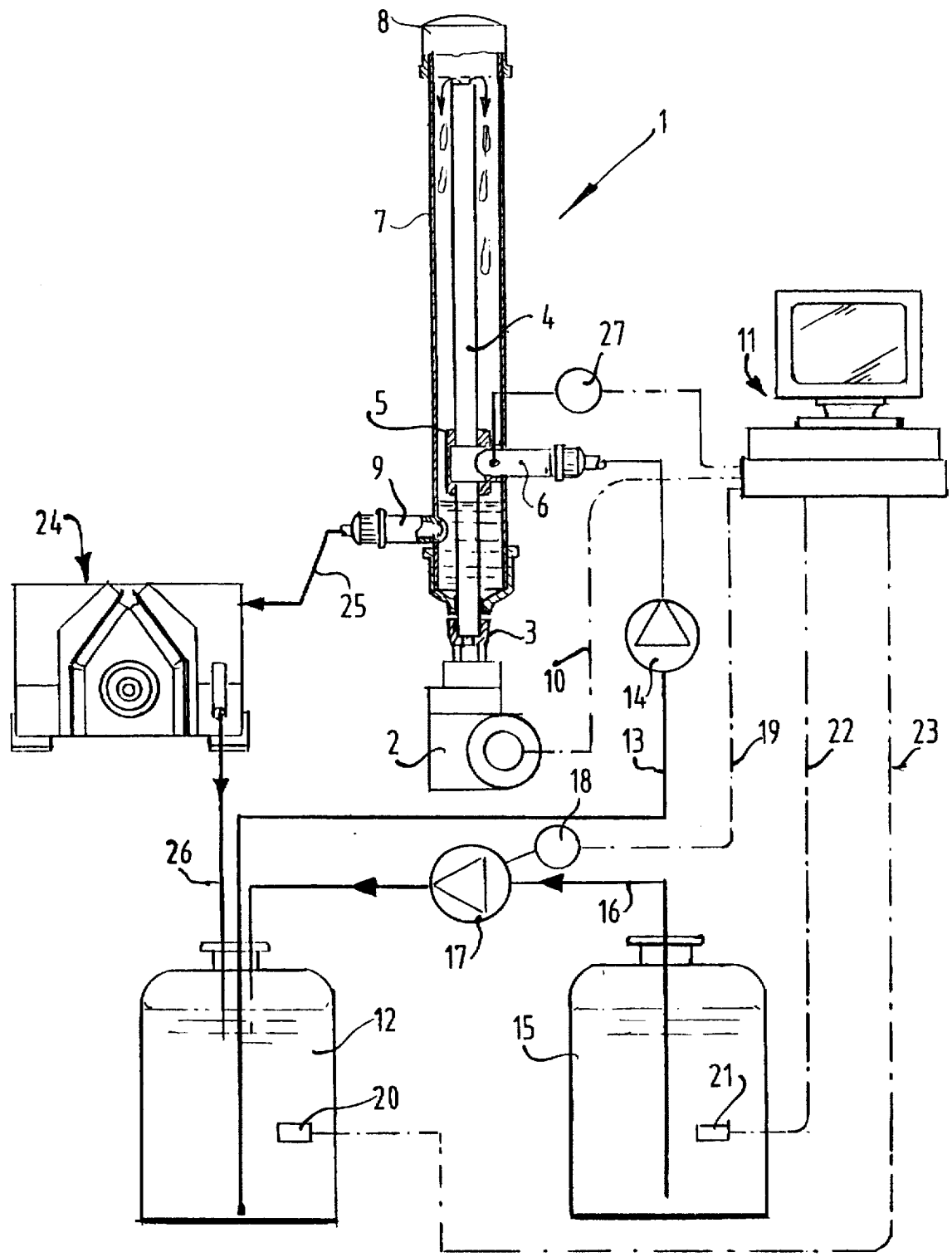

SOLDER FLUXER WITH LIQUID FLUX DENSITY CONTROL

BACKGROUND OF THE INVENTION

The invention relates to a device for determining the density of a liquid.

Such devices are necessary for instance in processes wherein use is made of a liquid, said process being particularly sensitive to the density of the liquid. Such a situation occurs for instance in the case of liquids used as flux in soldering apparatus or for instance in the case of printing inks. These are usually liquids provided with a diluent which evaporates quickly. In order to sustain as far as possible the quality of the process it is important that it process be carried out with a liquid with the most constant possible density. There is therefore a need for a liquid density measuring device.

SUMMARY OF THE INVENTION

The invention meets such a requirement by providing a device for determining the density of a liquid characterized by a liquid pressure measuring device; a measuring vessel extending above the level of the liquid pressure measuring device and connected to the liquid pressure measuring device; means for maintaining a constant liquid level in the measuring vessel; supply means for supplying the liquid for measuring to the measuring vessel; and draining means for draining from the measuring vessel the liquid whereof the density has been measured.

According to a preferred embodiment the means for maintaining a constant liquid level are formed by an overflow edge.

According to another preferred embodiment the horizontal surface of the measuring vessel is small compared to the height of the measuring vessel and the supply means are adapted to supply the liquid to the measuring vessel respectively drain the liquid from the measuring vessel continuously.

The invention likewise provides an apparatus for producing a dilutable liquid with the most constant possible density, characterized by a storage container; a liquid density measuring device connected to the storage container; means for supplying diluent to the storage container; and means for controlling the quantity of diluent to the storage container, wherein the output signal of the density measuring device is used to control the quantity of diluent to be supplied to the storage container.

BRIEF DESCRIPTION OF THE DRAWING

The invention will be elucidated hereinbelow with reference to the annexed FIGURE which shows a schematic view of an apparatus for producing a liquid with a constant density which is provided with a device for measuring the density of a liquid.

DETAILED DESCRIPTION OF A PREFERRED EMBODIMENT

The device shown in the FIGURE is formed by a liquid density meter designated in its entirety. The liquid density measuring device 1 is formed by a liquid pressure measuring device 2, of which the liquid pressure measuring device connecting piece 3 is connected to a vertically extending pipe 4. At its top, pipe 4 is open. In the proximity of the bottom end of pipe 4, a sleeve 5 is arranged around the pipe and is provided with a connecting piece 6 with which liquid can be supplied to the pipe 4.

Around pipe 4 and around sleeve 5 is further arranged a substantially cylindrical casing 7 through which connecting piece 6 extends. The casing 7 is provided on its top with a cover 8. This latter is provided with a hole in respect of pressure equalization. A drain connecting piece 9 is arranged on the underside of the casing. As shown in the FIGURE, the diameter of pipe 4 is small compared to its height and may be substantially the same diameter as the diameter of connecting piece 6.

The components described up to this point form the liquid density measuring device.

The liquid of which the density must be measured is supplied via the connecting piece 6. The liquid passes via sleeve 5 into pipe 4, runs initially downward onto the liquid pressure measuring device and then fills the pipe. The pipe is filled up to the level of sleeve 5 but eventually to the full level of pipe 4, whereby with a continued supply the liquid will flow over the upper edge of pipe 4. As a result of this operation a column with a constant height rests on liquid pressure measuring device 2. A constant volume of liquid thus also rests on the liquid pressure measuring device and the value of the pressure measured by the liquid pressure measuring device is a measure for the density of the liquid.

With a constant supply the liquid the liquid flowing over the upper edge of pipe 4 will be collected inside casing 7. The liquid level will initially rise inside casing 7 until it is above the level above of the drain connecting piece, whereafter the liquid will be drained via the drain connecting piece 9.

Connected to the liquid pressure measuring device 2 via a cable 10 is a computer which is adapted to process the momentary value of the measurement values generated by the liquid pressure measuring device. Thus obtained is a liquid density measuring device according to the present invention.

It is noted herein that this measuring device is suitable for a continuous supply and drain of liquid. It is equally possible to use the liquid density measuring device with a stepwise or batchwise supply or draining of liquid.

It is possible particularly in this latter case to give the pipe 4 a wider form so that the density of larger amounts of liquid can be determined in one operation.

The liquid density measuring device shown in the FIGURE forms part of an apparatus for producing liquid with a constant density.

This apparatus further comprises a storage container 12 for the liquid, in which the container is connected by means of a conduit 13 to the connecting piece 6, in which conduit 13 is arranged to a pump 14. Diluent is supplied from a diluent container 15 which is connected to storage container 12 by means of a conduit 16. Arranged in conduit 16 is a pump 17 which is driven by a motor 18 which can be controlled by computer 11 by means of control line 19. The operation of the apparatus described up to this point is as follows: The liquid pumped up continuously by pump 14 from container 12 is fed via a conduit 13 and connecting piece 6 to the liquid density measuring device 1, where the density of the liquid is measured. The liquid is subsequently drained via the drain connecting piece 9. The measurement signal present at the output terminal of the liquid pressure measuring device 2 is supplied via line 10 to computer 11 which, on the basis of the value of the signal, optionally controls the feed of diluent to storage container 12 by controlling the motor 18 and pump 17. By accurately measuring the density of the liquid it thus already becomes possible in the case of small variations, i.e. when the density is excessive, to add extra diluent so that the original target value is achieved as closely as possible.

The computer 11 further serves as level monitoring device. Placed for this purpose in each of the containers 12,15 is a level detector 20,21 respectively connected to the computer via lines 22,23 respectively. When a certain lowest value is approached an alarm can thus be given.

The present embodiment is an apparatus for preparing flux with a constant density for use in a flux unit for applying a layer of flux (soldering-enhancing liquid) to objects for soldering. Arranged herein is a fluxer 24 for supplying flux to the fluxer between the drain connecting piece 9 and the fluxer 24 via conduit 25. A conduit 26 is arranged for discharge of excess flux from the fluxer to the storage container.

Particularly this latter option, i.e. discharge of excess flux from the fluxer, results in the need for a device to maintain a constant flux.

Because the density of the flux is in large measure temperature-dependent, a thermometer 27 is arranged in the shown preferred embodiment close to the liquid density measuring device, and in particular close to the connecting piece 6, in order to measure the temperature of the supplied liquid. This thermometer is of course connected to the computer so that the latter can compensate the density values for the temperature.

I claim:

1. An apparatus for applying solder enhancing liquid flux to objects for soldering, including a fluxer and means to control the density of the liquid flux supplied to the fluxer, comprising:

a liquid flux storage container;

means to supply said liquid flux from said container to said fluxer;

a device for determining the density of the liquid flux supplied to said fluxer, said device being intermediate said liquid flux storage container and said fluxer and being capable of producing an output signal indicative of the determined density;

means to supply diluent to said storage container;

means to control the quantity of diluent supplied to said liquid flux storage container based on said output signal of the density determining device;

said density determining device including in combination:

a liquid flux pressure measurer;

a measuring vessel extending above and directly connected to the liquid flux pressure measurer, said vessel including means to maintain a constant flux liquid level therein; and draining means for draining the liquid flux from the vessel and directly supplying said flux from said vessel to said fluxer.

2. The apparatus as claimed in claim 1, characterized in that the means for maintaining a constant flux liquid level are formed by an overflow edge.

3. The apparatus as claimed in claim 2, characterized in that the diameter of the measuring vessel is small compared to the height of the measuring vessel.

4. The apparatus as claimed in claim 1, characterized in that the means to supply liquid flux and the draining means are adapted to supply the liquid flux to the measuring vessel and to drain the liquid flux from the measuring vessel continuously.

5. The apparatus as claimed in claim 4, characterized in that the diameter of the measuring vessel lies in the same order of magnitude as the diameter of the supply means to supply liquid flux leading to the measuring vessel.

6. The apparatus as claimed in claim 2, characterized in that the measuring vessel is placed in a casing, that the means to supply liquid flux comprise a supply pipe extending through the casing and connecting onto the measuring vessel, and that the draining means comprise a draining pipe connecting onto the casing.

7. The apparatus as claimed in claim 6, characterized in that the supply pipe is connected to the measuring vessel in and vicinity of the underside of the measuring vessel.

8. The apparatus as claimed in claim 1, characterized in that a thermometer is arranged close to the liquid density measuring device to measure the temperature of the liquid flux.

9. Apparatus as claimed in claim 1, characterized in that a pump is arranged between the storage container and the density measuring device, that the means for controlling the supply of diluent to the storage container are formed by a controllable pump and that the pumps are controlled by a computer to which the signal from the density measuring device is carried.

* * * * *